United States Patent
Chirik et al.

(10) Patent No.: US 10,112,961 B2
(45) Date of Patent: Oct. 30, 2018

(54) HYDROBORATION AND BORYLATION WITH COBALT CATALYSTS

(71) Applicant: THE TRUSTEES OF PRINCETON UNIVERSITY, Princeton, NJ (US)

(72) Inventors: Paul J. Chirik, Princeton, NJ (US); Tianning Diao, Sichuan (CN); Renyuan Yu, Beijing (CN)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 15/037,954

(22) PCT Filed: Nov. 19, 2014

(86) PCT No.: PCT/US2014/066422
§ 371 (c)(1),
(2) Date: May 19, 2016

(87) PCT Pub. No.: WO2015/077344
PCT Pub. Date: May 28, 2015

(65) Prior Publication Data
US 2016/0297838 A1    Oct. 13, 2016

Related U.S. Application Data

(60) Provisional application No. 61/906,204, filed on Nov. 19, 2013, provisional application No. 62/031,463, filed on Jul. 31, 2014.

(51) Int. Cl.
| | |
|---|---|
| *C07F 15/00* | (2006.01) |
| *C07F 5/02* | (2006.01) |
| *B01J 31/22* | (2006.01) |
| *C07F 19/00* | (2006.01) |
| *C07F 7/18* | (2006.01) |
| *C07F 15/06* | (2006.01) |
| *C07F 7/08* | (2006.01) |
| *B01J 31/18* | (2006.01) |

(52) U.S. Cl.
CPC ............ *C07F 5/025* (2013.01); *B01J 31/183* (2013.01); *B01J 31/2295* (2013.01); *C07F 7/0856* (2013.01); *C07F 7/0879* (2013.01); *C07F 7/184* (2013.01); *C07F 7/1876* (2013.01); *C07F 15/06* (2013.01); *C07F 19/00* (2013.01); *B01J 2231/14* (2013.01); *B01J 2231/323* (2013.01); *B01J 2531/845* (2013.01)

(58) Field of Classification Search
CPC .......... B01J 31/00; B01J 2231/00; C07F 7/00; C07F 15/06; C07F 19/00
USPC ....................................................... 556/138
See application file for complete search history.

(56) References Cited

U.S. PATENT DOCUMENTS

| | | | | |
|---|---|---|---|---|
| 5,827,794 | A * | 10/1998 | Davis ................... | B01J 31/0202 502/162 |
| 6,451,938 | B1 * | 9/2002 | Fisher ..................... | C08F 10/00 502/117 |
| 2008/0071047 | A1 * | 3/2008 | Solan ..................... | B01J 31/182 526/130 |
| 2011/0151586 | A1 | 6/2011 | Chen et al. | |
| 2012/0052423 | A1 * | 3/2012 | Maruyama ........... | G03G 5/0521 430/56 |

OTHER PUBLICATIONS

Hartwig et al., J. Amer. Chem Soc., 2008, 130:7534.*
Hartwig et al., J. Amer. Chem Soc., 2005, 127:14263.*
After Final Response—cover (Year: 2018).*
International Search Report and Written Opinion issued in corresponding International Application No. PCT/US2014/066422 dated Jan. 26, 2015, 5 pages.
Colak et al., Supramolecular colbalt(II)-pyridine-2,5-dicarboxylate complexes with isonicotinamide, 2-amino-3-methylpyridine and 2-amino-6-methylpyridine: Syntheses, crystal structures, spectroscopic, thermal and antimicrobial activity studies, Inorganica Chimica Acta 363 (2010), pp. 2149-2162.
Forster, D., Contact and Dipolar NMR Shifts in Nickel and Cobalt Pyridine Complexes, Inorganica Chimica Acta, vol. 5, Mar. 1971, pp. 465-468.
Keeton et al., A Variable Temperature Study of the Vibrational (far-infrared) and Electronic Spectra of Substituted Pyridine Cobalt(II) Halides. Evidence for Bond Weakening as a Function of Substitution, Spectrochimica Acta, vol. 26A, pp. 2173-2178.

* cited by examiner

*Primary Examiner* — Clinton A Brooks
*Assistant Examiner* — Kofi Adzamli
(74) *Attorney, Agent, or Firm* — J. Clinton Wimbish; Nexsen Pruet, PLLC

(57) ABSTRACT

In one aspect, cobalt complexes are described herein. In some embodiments, such cobalt complexes are operable as catalysts for hydroboration and borylation applications.

14 Claims, 6 Drawing Sheets

FIG. 3

HYDROBORATION AND BORYLATION WITH COBALT CATALYSTS

RELATED APPLICATION DATA

This application is a U.S. National Phase of PCT/US2014/066422, filed Nov. 19, 2014, which claims priority pursuant to 35 U.S.C. § 119(e) to U.S. Provisional Patent Application Ser. No. 61/906,204 filed Nov. 19, 2013 and U.S. Provisional Patent Application Ser. No. 62/031,463 filed Jul. 31, 2014, each of which is incorporated herein by reference in its entirety.

STATEMENT OF GOVERNMENT RIGHTS

The present invention was made with government support under National Science Foundation Grant Number CHE-1265988. The United States Government has certain rights to the present invention.

FIELD

The present invention relates to cobalt complexes and, in particular, to use of cobalt complexes as catalysts for hydroboration and borylation applications.

BACKGROUND

Organoboronates are a valuable class of reagents owing to their stability, ease of handling and versatility in various carbon-carbon and carbon heteroatom bond-forming reactions. Metal-catalyzed alkene hydroboration has proven an effective route to alkylboronates through precious metal catalysts with rhodium and iridium being the most common. In many instances, such precious metal catalysts are cost prohibitive for large scale operations. Therefore, attention has turned to catalysts based on more abundant transition metals, including first row transition metals. In addition to their potential economic and environmental benefits, catalysts based on first row transition metals, by virtue of the smaller atomic radii and unique electronic structures, have the potential to promote new chemistry or expand substrate scope not encountered with traditional metal catalysts.

SUMMARY

In one aspect, cobalt complexes are described herein. In some embodiments, such cobalt complexes are operable as catalysts for hydroboration and/or borylation applications. In some embodiments, a cobalt complex described herein is of Formula (I):

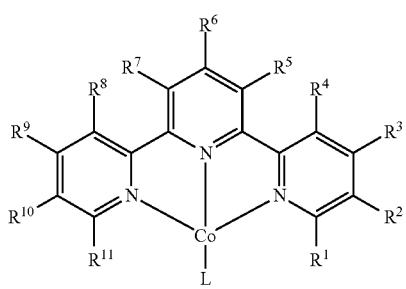

wherein $R^1$-$R^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$)-alkyl, ($C_1$-$C_{10}$)-alkenyl, alkoxy, halo, hydroxy, C(O)OR$^{12}$, NR$^{13}$R$^{14}$, wherein $R^{12}$-$R^{14}$ are independently selected from the group consisting of hydrogen, ($C_1$-$C_{10}$)-alkyl and ($C_1$-$C_{10}$)-alkenyl and wherein L is selected from the group consisting of alkyl, heteroalkyl, aryl, heteroaryl, alkyl-aryl, alkyl-heteroaryl, aryl-alkyl and heteroaryl-alkyl. In some embodiments, L is heteroalkyl of formula

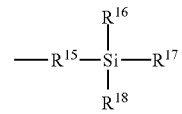

wherein $R^{15}$ is selected from the group consisting of alkyl, alkenyl, aryl, heteroaryl, alkyl-aryl, alkyl-heteroaryl, arylalkyl and heteroaryl-alkyl and $R^{16}$-$R^{18}$ are independently selected from the group consisting of hydrogen, alkyl, alkenyl, aryl, alkyl-aryl, alkoxy and hydroxy. For example, in some embodiments, L is —$CH_2$—Si($CH_3$).

In other embodiments, a cobalt complex described herein is of Formula (II):

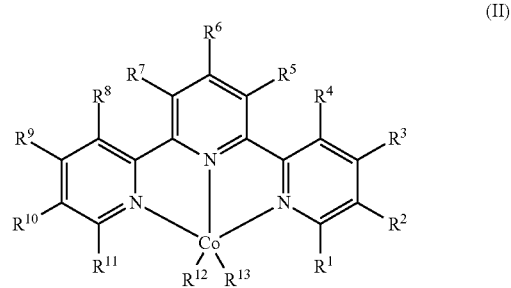

wherein $R^1$-$R^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of ($C_1$-$C_{10}$-alkyl, ($C_1$-$C_{10}$)-alkenyl, alkoxy, halo, hydroxy, C(O)OR$^{14}$, NR$^{15}$R$^{16}$, wherein $R^{14}$-$R^{16}$ are independently selected from the group consisting of hydrogen, ($C_1$-$C_{10}$)-alkyl and ($C_1$-$C_{10}$)-alkenyl and wherein $R^{12}$ and $R^{13}$ are independently selected from the group consisting of alkyl, alkylsilane and halo. In some embodiments, $R^{12}$ and $R^{13}$ are halo. For example, $R^{12}$ and $R^{13}$ can be selected as chloro.

In another aspect, methods of providing a hydroboration product employing cobalt catalysts are described herein. A method of providing a hydroboration product comprises providing a reaction mixture comprising an unsaturated compound having at least one unsaturated functional group, a hydroborating reagent and a cobalt complex and reacting the hydroborating reagent with the unsaturated compound in the presence of the cobalt complex or a derivative thereof, the cobalt complex having Formula (I):

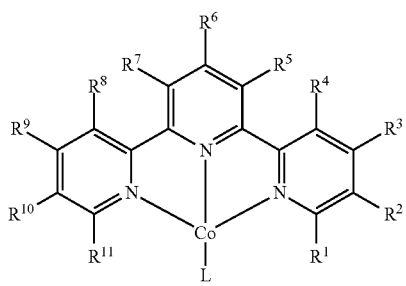

(I)

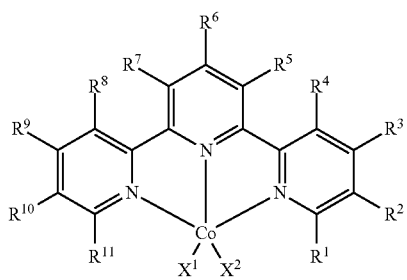

(IV)

wherein R$^1$-R$^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of (C$_1$-C$_{10}$)-alkyl, (C$_1$-C$_{10}$)-alkenyl, alkoxy, halo, hydroxy, C(O)OR$^{12}$, NR$^{13}$R$^{14}$, wherein R$^{12}$-R$^{14}$ are independently selected from the group consisting of hydrogen, (C$_1$-C$_{10}$)-alkyl and (C$_1$-C$_{10}$)-alkenyl and wherein L is selected from the group consisting of alkyl, heteroalkyl, aryl, heteroaryl, alkyl-aryl, alkyl-heteroaryl, aryl-alkyl and heteroaryl-alkyl.

In another aspect, methods of providing a borylated product employing cobalt catalysts are described herein. For example, a method of providing a borylated product comprises providing a reaction mixture comprising cobalt halide and ligand of Formula (III):

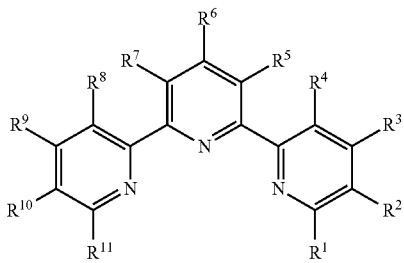

(III)

wherein R$^1$-R$^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of (C$_1$-C$_{10}$)-alkyl, (C$_1$-C$_{10}$)-alkenyl, alkoxy, halo, hydroxy, C(O)OR$^{12}$, NR$^{13}$R$^{14}$, wherein R$^{12}$-R$^{14}$ are independently selected from the group consisting of hydrogen, (C$_1$-C$_{10}$)-alkyl and (C$_1$-C$_{10}$)-alkenyl. The cobalt halide is reacted with the ligand of Formula (III) to form a cobalt complex. Activator is added to the reaction mixture to activate the cobalt complex, and an aliphatic compound or aromatic compound and borylation reagent of the reaction mixture are reacted in the presence of the activated cobalt complex or a derivative of the activated cobalt complex. In some embodiments, the cobalt complex formed by reaction of the ligand and cobalt halide is of Formula (IV):

wherein X$^1$ and X$^2$ are independently halo and R$^1$-R$^{11}$ are the same as in Formula (III).

In another embodiment, a method of providing a borylated product comprises providing a reaction mixture comprising an aliphatic compound or an aromatic compound, a borylation reagent and a cobalt complex having Formula (IV) hereinabove. Activator is added to the reaction mixture to activate the cobalt complex, and the aliphatic compound or aromatic compound is reacted with the borylation reagent in the presence of the activated cobalt complex or a derivative of the activated cobalt complex.

In a further aspect, methods of making cobalt complexes are described herein. A method of making a cobalt complex, in some embodiments, comprises providing a solution of py$_2$Co(R$^{15}$)(R$^{16}$) and adding to the solution a ligand Formula (III):

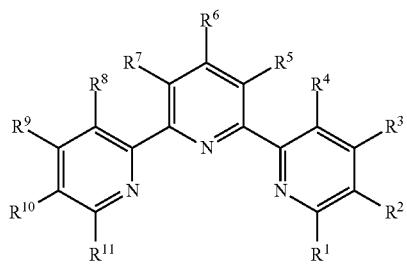

(III)

wherein R$^1$-R$^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of (C$_1$-C$_{10}$)-alkyl, alkoxy, halo, hydroxy, C(O)OR$^{12}$, NR$^{13}$R$^{14}$, wherein R$^{12}$-R$^{14}$ are independently selected from the group consisting of hydrogen, (C$_1$-C$_{10}$)-alkyl and (C$_1$-C$_{10}$)-alkenyl and wherein R$^{15}$ and R$^{16}$ are independently selected from the group consisting of alkyl, heteroalkyl, aryl, heteroaryl, alkyl-aryl and alkyl-heteroaryl. The pyridine ligands of py$_2$Co(R$^{15}$)(R$^{16}$) are subsequently displaced by the ligand of Formula (III).

These and other embodiments are described in further detail in the detailed description which follows.

BRIEF DESCRIPTION OF THE DRAWINGS

FIG. 3 illustrates a hydroboration reaction scheme catalyzed by a cobalt complex and resulting hydroboration products according to one embodiment described herein.

DETAILED DESCRIPTION

Figure 1:
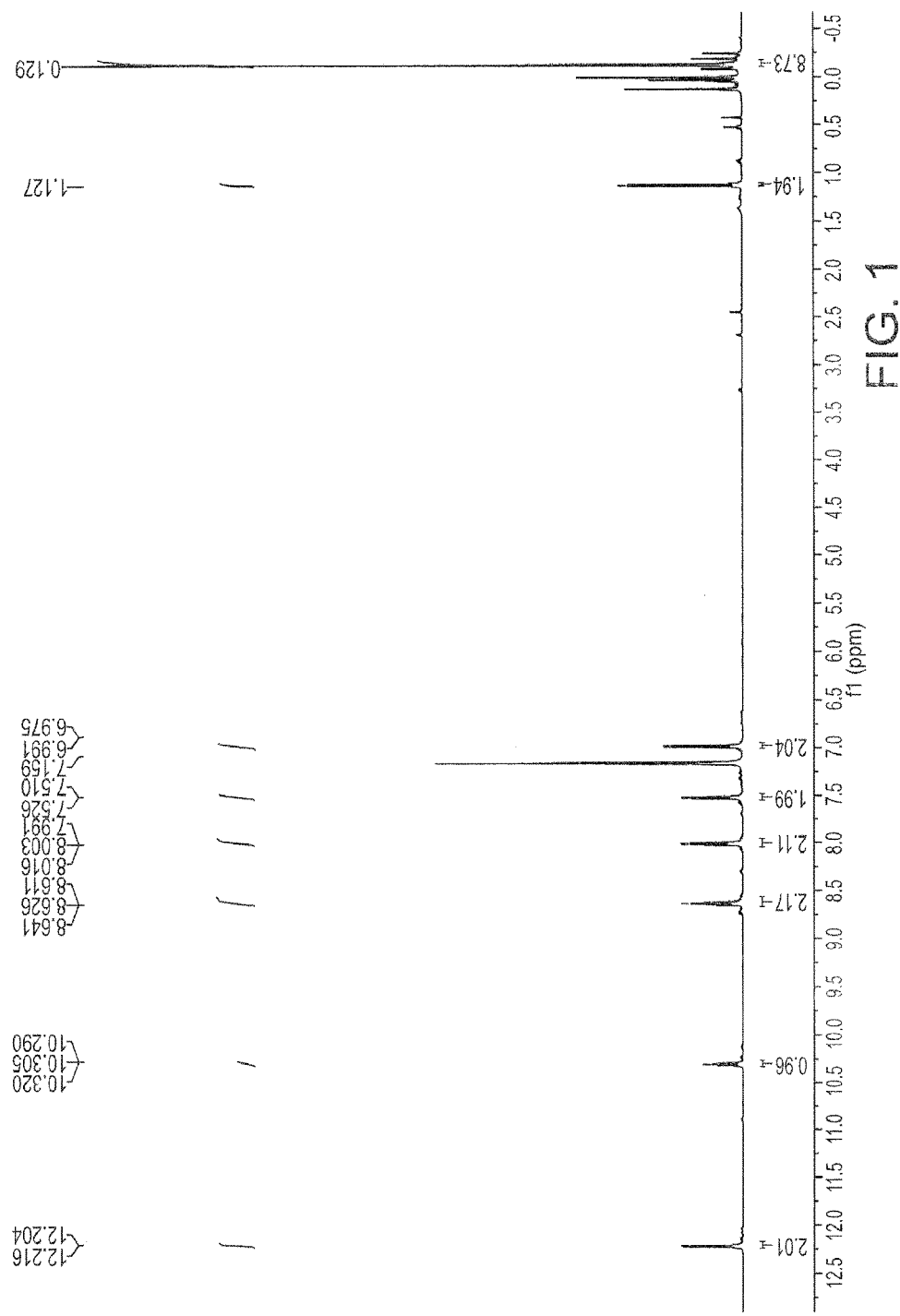
FIG. 1 is a $^1$H NMR spectrum of a cobalt complex according one embodiment described herein.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

Definitions

The term "alkyl" as used herein, alone or in combination, refers to a straight or branched saturated hydrocarbon group optionally substituted with one or more substituents. For example, an alkyl can be $C_1$-$C_{30}$.

The term "alkenyl" as used herein, alone or in combination, refers to a straight or branched chain hydrocarbon group having at least one carbon-carbon double bond and optionally substituted with one or more substituents The term "aryl" as used herein, alone or in combination, refers to an aromatic monocyclic or multicyclic ring system optionally substituted with one or more ring substituents.

The term "heteroaryl" as used herein, alone or in combination, refers to an aromatic monocyclic or multicyclic ring system in which one or more of the ring atoms is an element other than carbon, such as nitrogen, oxygen and/or sulfur.

The term "cycloalkyl" as used herein, alone or in combination, refers to a non-aromatic, mono- or multicyclic ring system optionally substituted with one or more ring substituents.

The term "heterocycloalkyl" as used herein, alone or in combination, refers to a non-aromatic, mono- or multicyclic ring system in which one or more of the atoms in the ring system is an element other than carbon, such as nitrogen, oxygen or sulfur, alone or in combination, and wherein the ring system is optionally substituted with one or more ring substituents.

The term "heteroalkyl" as used herein, alone or in combination, refers to an alkyl moiety as defined above, having one or more carbon atoms in the chain, for example one, two or three carbon atoms, replaced with one or more heteroatoms, which may be the same or different, where the point of attachment to the remainder of the molecule is through a carbon atom of the heteroalkyl radical.

The term "alkoxy" as used herein, alone or in combination, refers to the moiety RO—, where R is alkyl or alkenyl defined above.

The term "halo" as used herein, alone or in combination, refers to elements of Group VIIA of the Periodic Table (halogens). Depending on chemical environment, halo can be in a neutral or anionic state.

I. Cobalt Complexes

In one aspect, cobalt complexes are described herein. In some embodiments, such cobalt complexes are operable as catalysts for hydroboration and/or borylation applications. In some embodiments, a cobalt complex described herein is of Formula (I):

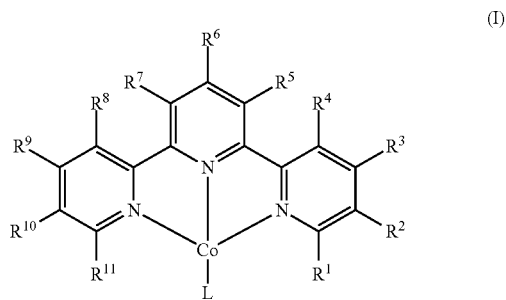

(I)

wherein $R^1$-$R^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR^{12}$, $NR^{13}R^{14}$, wherein $R^{12}$-$R^{14}$ independently selected from the group consisting of hydrogen, $(C_1$-$C_{10})$-alkyl and $(C_1$-$C_{10})$-alkenyl and wherein L is selected from the group consisting of alkyl, heteroalkyl, aryl, heteroaryl, alkyl-aryl, alkyl-heteroaryl, aryl-alkyl and heteroaryl-alkyl. In some embodiments, L is heteroalkyl of formula

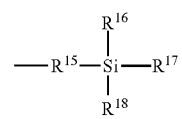

wherein $R^{15}$ is selected from the group consisting of alkyl, alkenyl, aryl, heteroaryl, alkyl-aryl, alkyl-heteroaryl, aryl-alkyl and heteroaryl-alkyl and $R^{16}$-$R^{18}$ are independently selected from the group consisting of hydrogen, alkyl, alkenyl, aryl, alkyl-aryl, alkoxy and hydroxy. For example, in some embodiments, L is —$CH_2$—$Si(CH_3)_3$.

In other embodiments, a cobalt complex described herein is of Formula (II):

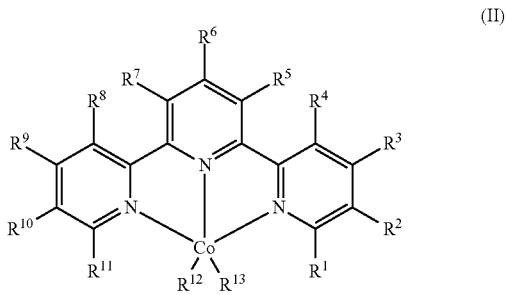

(II)

wherein $R^1$-$R^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1-C_{10})$-alkyl, $(C_1-C_{10})$-alkenyl, alkoxy, halo, hydroxy, $C(O)OR^{14}$, $NR^{15}R^{16}$, wherein $R^{14}$-$R^{16}$ are independently selected from the group consisting of hydrogen, $(C_1-C_{10})$-alkyl and $(C_1-C_{10})$-alkenyl and wherein $R^{12}$ and $R^{13}$ are independently selected from the group consisting of alkyl, alkylsilane and halo. In some embodiments, $X^1$ and $X^2$ are chloride.

II. Methods of Hydroboration

In another aspect, methods of providing a hydroboration product employing cobalt catalysts are described herein. A method of providing a hydroboration product comprises providing a reaction mixture comprising an unsaturated compound having at least one unsaturated functional group, a hydroborating reagent and a cobalt complex, and reacting the hydroborating reagent with the unsaturated compound in the presence of the cobalt complex or a derivative thereof, the cobalt complex having Formula (I):

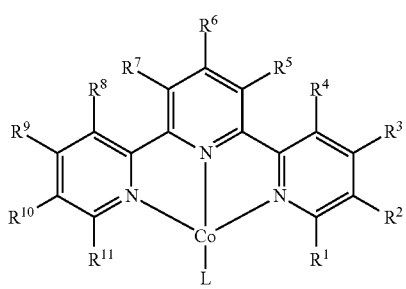

(I)

wherein $R^1$-$R^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1-C_{10})$-alkyl, $(C_1-C_{10})$-alkenyl, alkoxy, halo, hydroxy, $C(O)OR^{12}$, $NR^{13}R^{14}$, wherein $R^{12}$-$R^{14}$ are independently selected from the group consisting of hydrogen, $(C_1-C_{10})$-alkyl and $(C_1-C_{10})$-alkenyl and wherein L is selected from the group consisting of alkyl, heteroalkyl, aryl, heteroaryl, alkyl-aryl, alkyl-heteroaryl, aryl-alkyl and heteroaryl-alkyl. In some embodiments, L is heteroalkyl of formula

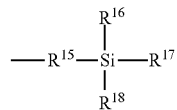

wherein $R^{15}$ is selected from the group consisting of alkyl, alkenyl, aryl, heteroaryl, alkyl-aryl, alkyl-heteroaryl, aryl-alkyl and heteroaryl-alkyl and $R^{16}$-$R^{18}$ are independently selected from the group consisting of hydrogen, alkyl, alkenyl, aryl, alkyl-aryl, alkoxy and hydroxy. For example, in some embodiments, L is —$CH_2$—$Si(CH_3)$.

The unsaturated functional group of the unsaturated compound is selected from the group consisting of a carbon-carbon double bond, carbon-carbon triple bond, carbon-nitrogen double bond and carbon-oxygen double bond. Non-limiting examples of such unsaturated compounds include ethylene, propylene, isobutylene, 1-hexene, 1-octene, 1-octadecene, styrene, alpha-methylstyrene, cyclopentene, norbornene, 1,5-hexadiene, norbornadiene, vinylcyclohexene, allyl alcohol, allyl-terminated polyethyleneglycol, allylacrylate, allyl methacrylate, allyl glycidyl ether, allyl-terminated isocyanate-or acrylate prepolymers, polybutadiene, allylamine, methallyl amine, acetylene, phenylacetylene, vinyl-pendent or vinyl-terminal polysiloxanes, vinylcyclosiloxanes, vinylsiloxane resins, vinyl-functional synthetic or natural minerals, etc. Additional olefins not inconsistent with the objectives of the present invention are also contemplated herein.

Further, the hydroborating reagent can be a boronic acid derivative. In some embodiments, a boronic acid derivative is selected from the group consisting of 4,4,5,5-tetramethyl-1,3,2-dioxaborolane, 4,6,6-trimethyl-1,3,2-dioxaborinane and catecholborane. Additionally, the hydroborating reagent can be a mono-substituted borane or di-substituted borane. Further, any solvent not inconsistent with the objectives of the present invention can be employed in the reaction mixture. Suitable solvent can be organic solvent, such as methyl tert-butyl ether (MTBE).

III. Methods of Borylation

In another aspect, methods of providing a borylated product employing cobalt catalysts are described herein. For example, a method of providing a borylated product comprises providing a reaction mixture comprising cobalt halide and ligand of Formula (III):

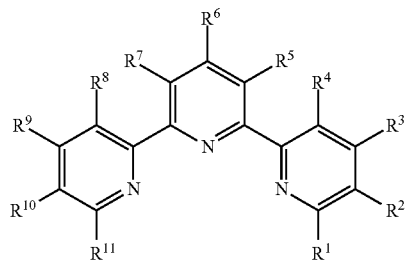

(III)

wherein $R^1$-$R^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1-C_{10})$-alkyl, $(C_1-C_{10})$-alkenyl, alkoxy, halo, hydroxy, $C(O)OR^{12}$, $NR^{13}R^{14}$, wherein $R^{12}$-$R^{14}$ are independently selected from the group consisting of hydrogen, $(C_1-C_{10})$-alkyl and $(C_1-C_{10})$-alkenyl. The cobalt halide is reacted with the ligand of Formula (III) to form a cobalt complex. Activator is added to the reaction mixture to activate the cobalt complex, and an aliphatic compound or aromatic compound and borylation reagent of the reaction mixture are reacted in the presence of the activated cobalt complex or a derivative of the activated cobalt complex. In some embodiments, the cobalt complex formed by reaction of the ligand and cobalt halide is of Formula (IV):

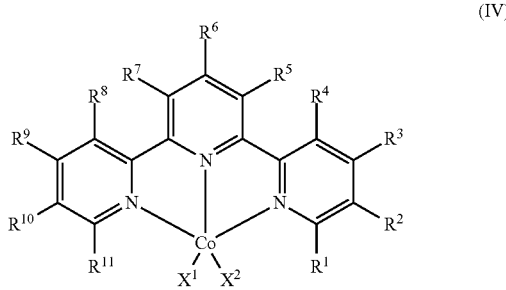

(IV)

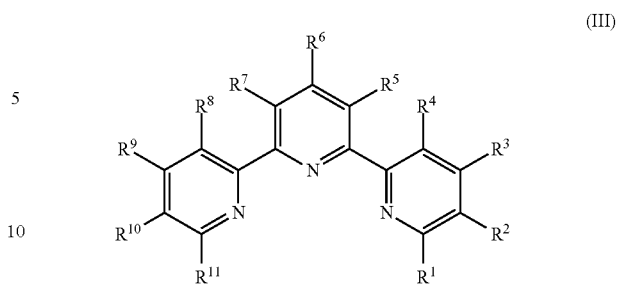

(III)

wherein $X^1$ and $X^2$ are independently halo and $R^1$-$R^{11}$ are the same as in Formula (III).

In some embodiments, the cobalt halide reacted with the ligand is cobalt chloride. Moreover, the borylation reagent can be a boronic acid derivative or a diboron compound. In some embodiments, the borylation reagent is selected from the group consisting of bis(pinacolato)diboron, bis(hexylene glycolato)diboron, bis(catecholato)diboron and bis(neopentyl glycolato)diboron. Aliphatic compounds in the borylation reaction can be saturated, unsaturated or alicyclic. Additionally, the aromatic compound can be aryl or heteroaryl. In some embodiments, the aromatic compound is a five-membered or six-membered ring. Further, any solvent not inconsistent with the objectives of the present invention can be employed in the reaction mixture. Suitable solvent can be organic solvent, such as tetrahydrofuran (THF).

Any activator operable to place the cobalt complex in a catalytic state for the borylation can be used. In some embodiments, suitable activator is a borohydride, including alkyl-substituted boron hydrides. As described further herein, an activator can be an alkali triethylborohydride. The activator can be present in the reaction mixture in any amount not inconsistent with the objectives of the present invention.

Importantly, the aliphatic compound or aromatic compound and/or borylation reagent can be present in the reaction mixture during reaction of the ligand and cobalt halide forming the cobalt complex. Alternatively, the aliphatic compound or aromatic compound and/or borylation reagent can be added to the reaction mixture subsequent to formation of the cobalt complex. In some embodiments, the reaction mixture in which the cobalt complex is formed does not require further processing, such as purification or removal of unreacted species, prior to introduction of the activator for initiating the borylation reaction.

In another embodiment, a method of providing a borylated product comprises providing a reaction mixture comprising an aliphatic compound or an aromatic compound, a borylation reagent and a cobalt complex having Formula (IV) hereinabove. Activator is added to the reaction mixture to activate the cobalt complex, and the aliphatic compound or aromatic compound is reacted with the borylation reagent in the presence of the activated cobalt complex or a derivative of the activated cobalt complex.

IV. Methods of Producing Cobalt Complexes

In a further aspect, methods of making cobalt complexes are described herein. A method of making a cobalt complex, in some embodiments, comprises providing a solution of $py_2Co(R^{15})(R^{16})$ and adding to the solution a ligand Formula (III):

wherein $R^1$-$R^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR^{12}$, $NR^{13}R^{14}$, wherein $R^{12}$-$R^{14}$ are independently selected from the group consisting of hydrogen, $(C_1$-$C_{10})$-alkyl and $(C_1$-$C_{10})$-alkenyl and wherein $R^{15}$ and $R^{16}$ are independently selected from the group consisting of alkyl, heteroalkyl, aryl, heteroaryl, alkyl-aryl and alkyl-heteroaryl The pyridine ligands of $py_2Co(R^{15})(R^{16})$ are subsequently displaced by the ligand of Formula (III). In some embodiments, $R^{15}$ and $R^{16}$ are heteroalkyl. As illustrated further herein, $R^{15}$ and $R^{16}$ can each be —$CH_2$—$Si(CH_3)_3$.

In some embodiments, methods described herein further comprise ejecting $R^{15}$ or $R^{16}$ from the cobalt complex. Ejection of $R^{15}$ or $R^{16}$ to provide a four-coordinate cobalt complex can accompany displacement of the pyridine ligands by terpyridine or terpyridine derivative of Formula (III). Such ejection can occur concurrent with addition of the terpyridine ligand or occur subsequent to ligand addition during stirring of the reaction product mixture.

These and other embodiments are further illustrated by the following non-limiting examples.

General Considerations

All air- and moisture-sensitive manipulations were carried out using vacuum line, Schlenk and cannula techniques or in an MBraun inert atmosphere (nitrogen) dry box. All glassware was stored in a pre-heated oven prior to use. The solvents used in the dry box were dried and deoxygenated using literature procedures. Deuterated solvents (Cambridge Isotope Laboratories) and HBPin (Aldrich) were used without further purification. Solid olefins were dried under reduced pressure prior to use. Liquid olefins were dried on $CaH_2$ or $LiAlH_4$ and distilled under reduced pressure prior to use.

$^1H$ NMR spectra were recorded on either Bruker 300 and 500 spectrophotometers operating at 300 MHz, and 500 MHz, respectively, or a Varian 400 spectrophotometer operating at 400 MHz. $^{13}C$ NMR spectra were recorded on a Bruker 500 spectrometer operating at 126 MHz. All $^1H$ and $^{13}C$ NMR chemical shifts are reported relative to $SiMe_4$ using the $^1H$ (residual) and $^{13}C$ chemical shifts of the solvent as a secondary standard. The NMR spectra of all the hydroboration products were taken using $CDCl_3$ as the solvent unless otherwise specified. Carbons that are directly attached to boron atoms were not observed due to quadrupolar relaxation. The composition of product mixtures was determined by integration of characteristic peaks in the $^1H$ NMR or the quantitative $^{13}C$ NMR spectra. $^1H$ NMR spectra of diastereomeric products were not assigned because their NMR resonances overlap with each other. Only their $^{13}$C NMR spectra were assigned.

EXAMPLE 1

Preparation of (terpy)CoCH$_2$SiMe$_3$

A 20 mL scintillation vial was charged with 0.424 g (1.083 mmol) of (py)$_2$Co(CH$_2$SiMe$_3$)$_2$ and 10 mL of diethyl ether. While stirring, 0.253 g (1.083 mmol) 2,2';6',2"-terpyridine (terpy) was added and the resulting solution was allowed to stir at room temperature for 16 hours, during which time a color change from deep green to purple was observed. The solution was filtered through celite and concentrated in vacuo. The resulting residue was recrystallized from pentane to yield 0.329 g (80%) of (terpy)CoCH$_2$SiMe$_3$ as purple crystals. Anal Calcd for C$_{19}$H$_{22}$CoN$_3$Si: C, 60.15; H, 5.84; N, 11.07. Found: C, 59.72; H, 5.76; N, 10.91. $^1$H NMR (500 MHz, benzene-d$_6$, 23° C.) δ12.21 (d, J$_{HH}$=5.9 Hz, 2H, 6,6" C—H), 10.31 (t, J$_{HH}$=7.5 Hz, 1H, 4' C—H), 8.63 (app t, J$_{HH}$=7.6 Hz, 2H, 4,4" C—H), 8.00 (app t, J$_{HH}$=6.4 Hz, 2H, 5,5" C—H), 7.52 (d, J$_{HH}$=8.1 Hz, 2H, 3,3" C—H), 6.98 (d, J$_{HH}$=7.6 Hz, 2H, 3',5' C—H), 1.13 (s, 2H, CH$_2$SiMe$_3$), −0.13 (s, 9H, CH$_2$SiMe$_3$) ppm. $^{13}$C NMR (126 MHz, benzene-d$_6$, 23° C.): δ 162.2 (2,2" CH$_0$), 157.2 (CH$_1$, 6,6" C—H), 147.7 (2',6' CH$_0$), 129.7 (CH$_1$, 4,4" C—H), 125.8 (CH$_1$, 5,5" C—H), 125.2 (CH$_1$, 3',5' C—H), 124.4 (CH$_1$, 3,3" C—H), 111.9 (CH$_1$, 4' C—H), 3.5 (CH$_3$, CH$_2$SiMe$_3$) ppm.

Figure 2:
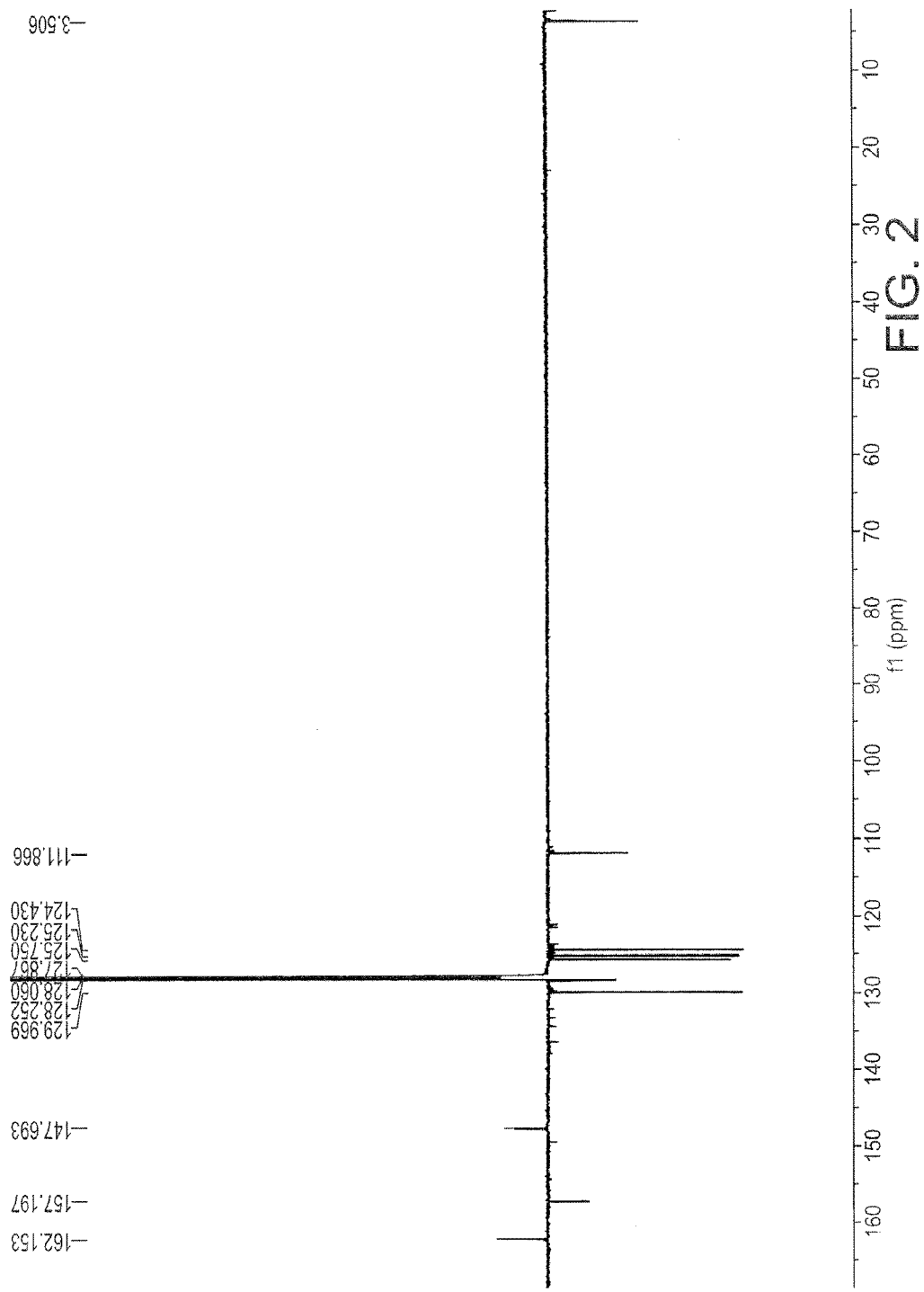
FIG. 2 is a $^{13}$C proton NMR spectrum of a cobalt complex according to one embodiment described herein.

$^1$H NMR and $^{13}$C NMR of the synthesized (terpy) CoCH$_2$SiMe$_3$ are provided in FIGS. 1 and 2 respectively.

EXAMPLE 2

Olefin Hydroboration with Cobalt Catalyst

General Procedure—In a typical experiment, a scintillation vial (with a magnetic stir bar) was charged in the glovebox with 0.64 mL tent-butyl methyl ether, 0.64 mmol (1 eq) of the desired olefin, 0.67 mmol (1.05 eq) of pinacolborane (HBPin), 0.64 mmol (1 eq) cyclooctane internal standard, and 1 mol % of the (terpy)CoCH$_2$SiMe$_3$ precatalyst. The vial was capped and the mixture was stirred at 23° C. until the reaction was complete. The reaction was monitored by analysis of aliquots by gas chromatography. Upon completion, the mixture was concentrated, diluted with hexane and passed through a silica plug in a Pasteur pipette and concentrated in vacuo. The resulting solution was concentrated and then analyzed by GC-FID, $^1$H NMR, and $^{13}$C NMR to determine the purity, identity, and regioisomeric and diastereomeric ratio of products. Partial conversions were determined by comparing the ratio of substrate to internal standard to the ratio obtained in an initial aliquot taken at the beginning of the reaction.

Figure 3:
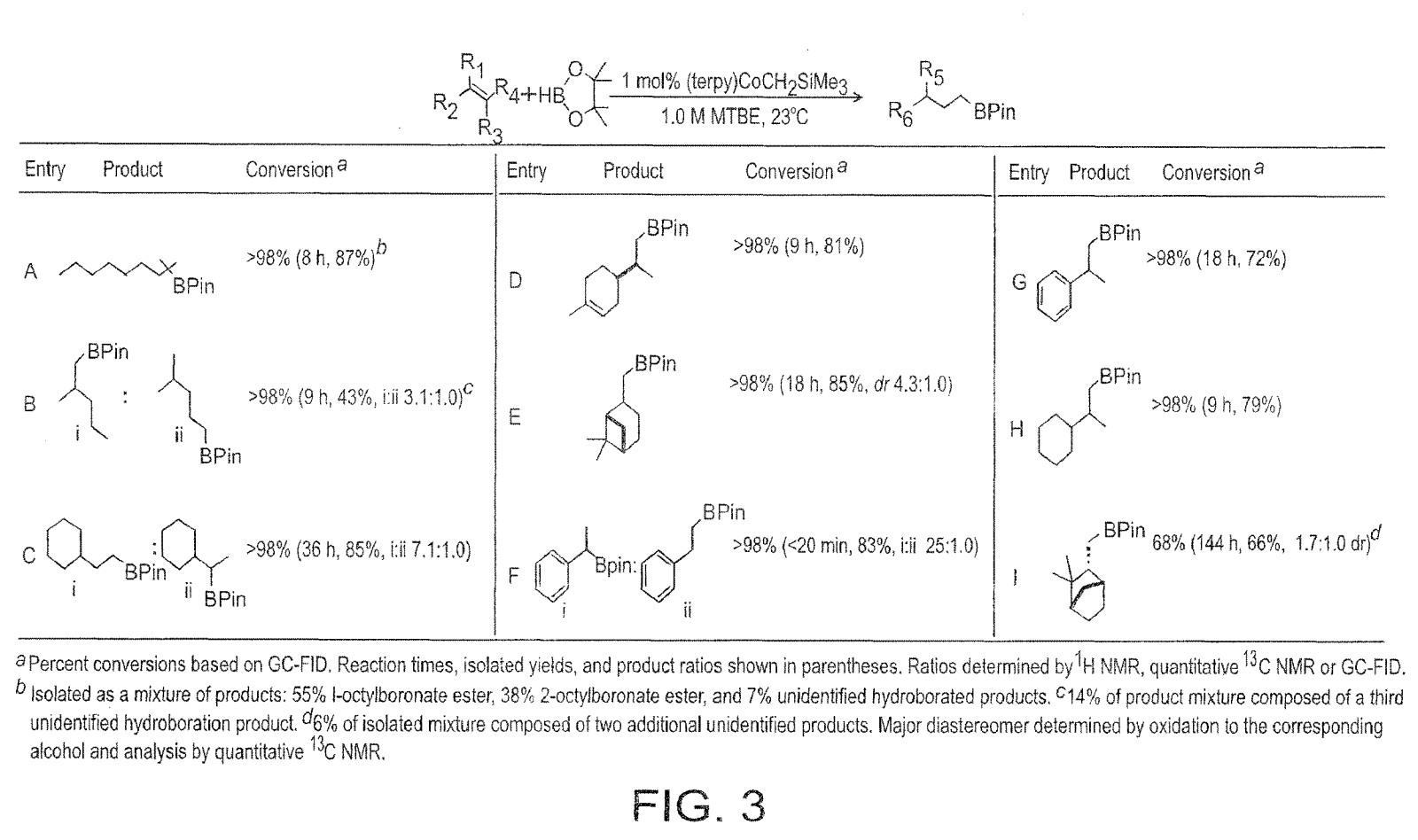

The foregoing hydroboration reaction scheme and resulting hydroboration products are illustrated in FIG. 3. Hydroboration products A-I provided according to this hydroboration scheme are further characterized below.

A

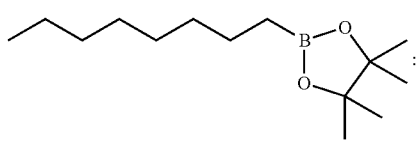

i

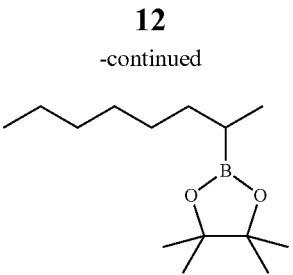

ii 2-octyl-4,4,5,5-tetramethyl-1,3,2-dioxaborolane (A-i). $^1$H NMR (500 MHz, chloroform-d, 23° C.): δ 1.42-1.35 (m, 2H), 1.31-1.16 (m, 10H), 1.25 (s, 12H), 0.84 (t, J=6.4 Hz, 3H), 0.74 (t, J=7.7 Hz, 2H) ppm. $^{13}$C NMR (126 MHz, chloroform-d, 23° C.): δ 83.0, 32.6, 32.1, 29.5, 29.4, 25.0, 24.2, 22.8, 14.3 ppm. $^1$H and $^{13}$C NMR data agree with previously reported data.

2-(2-octyl)-4,4,5,5-tetramethyl-1,3,2-dioxaborolane (A-ii). The $^1$H NMR spectrum was not assigned since the proton resonances could not be distinguished from those of regioisomer a, also present in the product mixture. $^{13}$C NMR (126 MHz, CDCl$_3$): δ 82.9, 33.4, 32.0, 29.7, 29.1, 24.9, 24.8, 22.8, 15.7, 14.3 ppm. $^1$H and $^{13}$C NMR data agree with previously reported data.

B

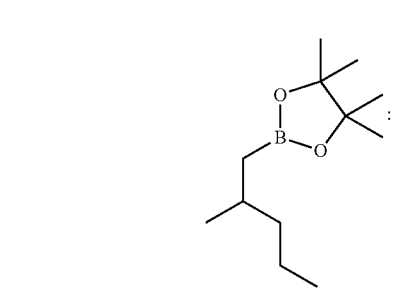

i

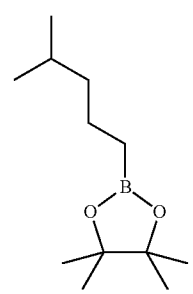

ii 2-(2-methylpentyl)-4,4,5,5-tetramethyl-1,3,2-dioxaborolane (B-i). The $^1$H NMR spectrum was not assigned because overlapping proton resonances from both regioisomers. $^{13}$C NMR (126 MHz, chloroform-d, 23° C.): δ 82.9, 42.2, 29.3, 25.0, 24,9, 22.5, 20.5, 14.5 ppm. $^1$H and $^{13}$C NMR data agree with previously reported data.

2-(4-methylpentyl)-4,4,5,5-tetramethyl-1,3,2-dioxaborolane (B-ii). The $^1$H NMR spectrum was not assigned because overlapping proton resonances from both diastereomers. $^{13}$C NMR (126 MHz, chloroform-d, 23° C.): δ 83.0, 42.1, 27,9, 24.9, 22.8, 21.9 ppm. $^1$H and $^{13}$C NMR data agree with previously reported data.

C

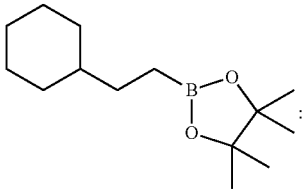

i

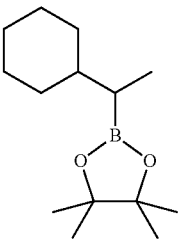

ii 2-(2-cyclohexylethyl)-4,4,5,5-tetramethyl-1,3,2-dioxaborolane (C-i). ¹H NMR (500 MHz, chloroform-d, 23° C.): ☐1.74-1.59 (m, 5H), 1.32-1.26 (m, 2H), 1.24 (s, 12H), 1.21-1.07 (m, 4H), 0.88-0.78 (m, 2H), 0.75 (t, 7.1 Hz, 2H) ppm. ¹³C NMR (126 MHz, chloroform-d, 23° C.): δ 83.0, 40.1, 33.1, 31.5, 26.9, 26.6, 25.0 ppm. ¹H and ¹³C NMR data agree with previously reported data.

2-(1-cyclohexylethyl)-4,4,5,5-tetramethyl-1,3,2-dioxaborolane (C-ii). The ¹H NMR spectrum was not assigned since the proton resonances are obscured by those of the major regioisomer a. ¹³C NMR (126 MHz, chloroform-d, 23° C.): δ 82.7, 40.5, 32.7, 31.9, 27.0, 26.8, 24.9, 24.8, 12.6 ppm. The ¹³C NMR data agree with previously reported data.

D

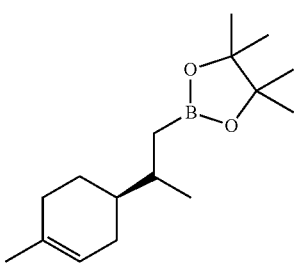

(+/−)-2-(2-(4-methylcyclohex-3-en-1-yl)propyl)-4,4,5,5-tetramethyl-1,3,2-dioxaborolane (D). Diastereomers of this compound were not distinguished by ¹H or ¹³C NMR due to overlapping resonances. ¹H NMR (500 MHz, chloroform-d, 23° C.): δ 5.36 (br s, 1H), 2.02-1.86 (m, 3H), 1.77-1.64 (m, 3H), 1.62 (s, 3H), 1.33-1.15 (m, 2H), 1.25 (s, 6H), 1.24 (s, 6H), 0.92-0.86 (m, 4H), 0.61 (dd, J$_{HH}$=15.3, 9.9 Hz, 1H) ppm. ¹³C NMR (126 MHz, chloroform-d, 23° C.): δ 134.0, 121.2, 83.0, 40.8, 34.0, 33.9, 31.1, 29.3, 28.5, 26.9, 26.0, 25.1, 24.9, 23.6, 19.5, 19.2 ppm. ¹H and ¹³C NMR data agree with previously reported data.

E

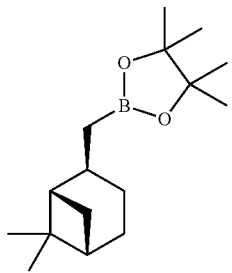

i ii 2-(((2R)-6,6-dimethylbicyclo[3.1.1]heptan-2-yl)methyl)-4,4,5,5-tetramethyl-1,3,2-dioxaborolane (E-i). The ¹H NMR spectrum was not assigned because overlapping proton resonances from both diastereomers. ¹³C NMR (126 MHz, chloroform-d, 23° C.): δ 82.9, 48.7, 40.8, 39.7, 38.9, 31.3, 27.0, 26.8, 24.9, 24.4, 23.2, 20.3 ppm. ¹H and ¹³C NMR data agree with previously reported data.

2-(42S)-6,6-dimethylbicyclo[3.1.1]heptan-2-yl)methyl)-4,4,5,5-tetramethyl-1,3,2-dioxaborolane (E-ii). The ¹H NMR spectrum was not assigned because overlapping proton resonances from both diastereomers. ¹³C NMR (126 MHz, chloroform-d, 23° C.): δ 82.9, 48.9, 41.4, 38.9, 37.4, 34.1, 28.4, 26.7, 25.0, 24.8, 24.4, 23.3 ppm. ¹H and ¹³C NMR data agree with previously reported data.

F

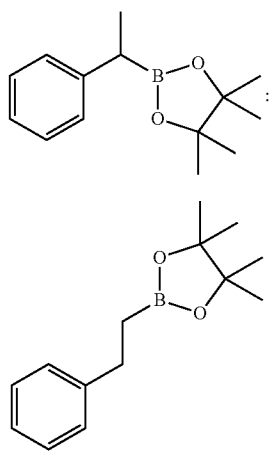

i ii 2-(1-phenethyl)-4,4,5,5-tetramethyl-1,3,2-dioxaborolane (F-i). ¹H NMR (500 MHz, chloroform-d, 23° C.): δ 7.29-7.20 (m, 4H), 7.16-7.11 (m, 1H), 2.44 (q, J$_{HH}$=7.4 Hz, 1H), 1.33 (d, J$_{HH}$=7.4 Hz, 3H), 1.22 (s, 6H), 1.20 (s, 6H) ppm. ¹³C NMR (126 MHz, chloroform-d, 23° C.): δ 145.1, 128.4, 127.9, 125.2, 83.4, 24.8, 24.7, 17.2 ppm. ¹H and ¹³C NMR data agree with previously reported data.

2-(2-phenethyl)-4,4,5,5-tetramethyl-1,3,2-dioxaborolane (F-ii). ¹H NMR (500 MHz, chloroform-d, 23° C.): δ 2,75 (t, $J_{HH}$=8.1 Hz), 1.24 (s, 12H) ppm. The remaining proton resonances were not assigned since they are obscured by those of the major regioisomer a. $^{13}$C NMR (126 MHz, chloroform-d, 23° C.): δ 144.5, 128.3, 128.1, 125.6, 83.2, 30.1, 24.9 ppm. $^1$H and $^{13}$C NMR data agree with previously reported data.

G

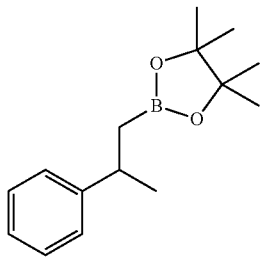

2-(2-phenylpropyl)-4,4,5,5-tetramethyl-1,3,2-dioxaborolane (G). $^1$H NMR (500 MHz, chloroform-d, 23° C.): δ 7.29-7.24 (m, 4H), 7.18-7.13 (m, 1H), 3.03 (app h, $J_{HH}$=7.1 Hz, 1H), 1.28 (d, $J_{HH}$ =7.0 Hz, 3H), 1.20 (m, 2H), 1.16 (s, 12H) ppm. $^{13}$C NMR (126 MHz, chloroform-d, 23° C.): δ 149.3, 128.3, 126.7, 125.8, 83.1, 35.9, 25.0, 24.9, 24.8 ppm. $^1$H and $^{13}$C NMR data agree with previously reported data.

H

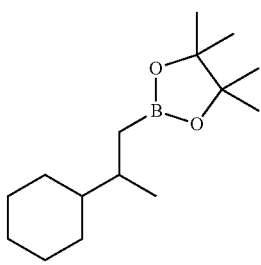

2-(2-cyclohexylpropyl)-4,4,5,5-tetramethyl-1,3,2-dioxaborolane (H).$^1$H NMR (500 MHz, chloroform-d, 23° C.): δ 75, 53 ppm, 6H), 1.25 (s, 6H), 1.24 (s, 6H), 1.18-1.03 (m, 4H), 1.00-0.86 (m, 2H), 0.86 (d, $J_{HH}$ =6.8 Hz, 3H), 0.82 (d, $J_{HH}$=4.6 Hz, 1H), 0.59 (dd, $J_{HH}$=9.8, 15.2 Hz, 1H) ppm. $^{13}$C NMR (126 MHz, chloroform-d, 23° C.): δ 82.9, 45.0, 34.7, 30.5, 29.3, 27.1, 27.0, 26.9, 25.1, 24.9, 19.3 ppm. $^1$H and $^{13}$C NMR data agree with previously reported data.

I

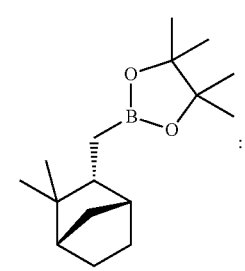

i

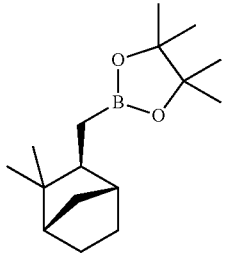

ii 2-4(2R)-3,3-dimethylbicyclo[2.2.1]heptan-2-yl-methyl)-4,4,5,5-tetramethyl-1,3,2-dioxaborolane (I-i). The mixture of diastereomers was isolated as a white solid. The $^1$H NMR spectrum was not assigned because overlapping proton resonances from both diastereomers. $^{13}$C NMR (126 MHz, chloroform-d, 23° C.): δ 82.9, 49.2, 46.1, 37.1, 32.1, 29.8, 25.0, 24.9, 24.8, 24.7, 22.0, 20.1 ppm. GCMS m/z (% relative intensity, ion) 251.9 (0.24%, M$^-$-12), 136.1 (4%, M$^+$-128) 121,1 (9%, M$^+$-143), 111.1 (7%, M$^+$-153), 93.1 (22%, M$^+$-171), 79.1 (10%, M$^+$-185), 67.1 (20%, M$^+$-197), 55.1 (8%, M$^+$-209), 41.1 (19%, M$^4$-223). The major diastereomer was determined by oxidation of the isolated mixture of diastereomers with $H_2O_2$ to the known alcohol diastereomers[8] and analysis of the quantitative $^{13}$C NMR spectrum.

2-(((2S)-3,3-dimethylbicyclo[2.2.1]heptan-2-yl-methyl)-4,4,5,5-tetramethyl-1,3,2-dioxaborolane (I-ii). The $^1$H NMR spectrum was not assigned because of overlap of the resonances between diastereomers. $^{13}$C NMR (126 MHz, chloroform-d, 23° C.): δ 82.9, 49.8, 49.4, 46.5, 40.7, 37.2, 35.5, 27.8, 25.0, 24.9, 25.6, 24.3 ppm.

EXAMPLE 3

Figure 4:
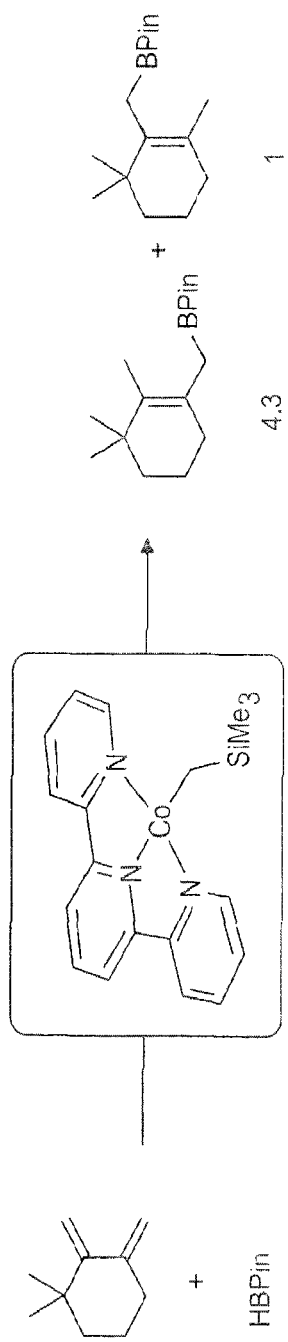
FIG. 4 illustrates a hydroboration reaction scheme with a cobalt complex according to one embodiment described herein.

Hydroboration of 1,3-diene (δ-pyronene)

δ-pyronene was subjected to hydroboration with HBPin in the presence of (terpy)CoCH$_2$SiMe$_3$ pre-catalyst as illustrated in the reaction scheme of FIG. 4. In a nitrogen filled glovebox, a scintillation vial was charged with a stir bar, 0.087 g (0.64 mmol) of δ-pyronene, 0.086 g (0.67 mmol) of HBPin, 0.006 g (0.016 mmol) of (terpy)CoCH$_2$SiMe$_3$ and 0.64 ml toluene. The vial was sealed with a cap and stirred at 23° C. for 16 hours. The reaction progress was monitored by GC-FID. Upon reaction completion, the mixture was concentrated, dissolved in hexane and filtered through a silica plug. The resulting solution was concentrated and analyzed by GC-FID, and $^1$H NMR spectroscopy to determine yield and purity.

EXAMPLE 4

Figure 5:
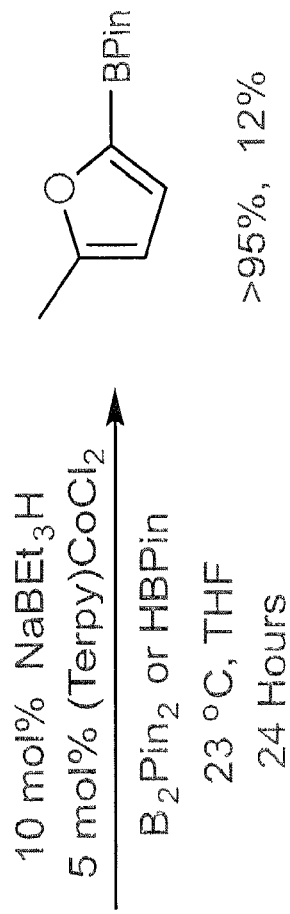
FIG. 5 illustrates a borylation reaction scheme according to one embodiment described herein.

Borylation with Co Catalyst 2-methylfuran was reacted with borylation reagent bis (pinacolato)diboron (B$_2$Pin$_2$) as illustrated in FIG. 5. In a nitrogen filled glovebox, a scintillation vile was charged with a stir bar, 0.140 g (0.5 mmol) of B$_2$Pin$_2$, 0.45 g (0.55 mm of 2-methyl furan, 1.0 ml of THF, 0.010 g (0.028 mmol, 0.05 equiv.) of (terpy)CoCl$_2$ and lastly, 0.055 ml (0.055 mmol, 0.1 equiv) of 1M sodium triethylborohydride in toluene. The vial was then capped and stirred for 24 hours at 23° C., after which the reaction was quenched by exposure to air. The solvent was evaporated in vacuo, and the residue was filtered through a plug of silica gel with hexane solution in vacuo. The isolated compound was analyzed by $^1$H NMR and $^{13}$C NMR spectroscopy.

EXAMPLE 5

Figure 6:
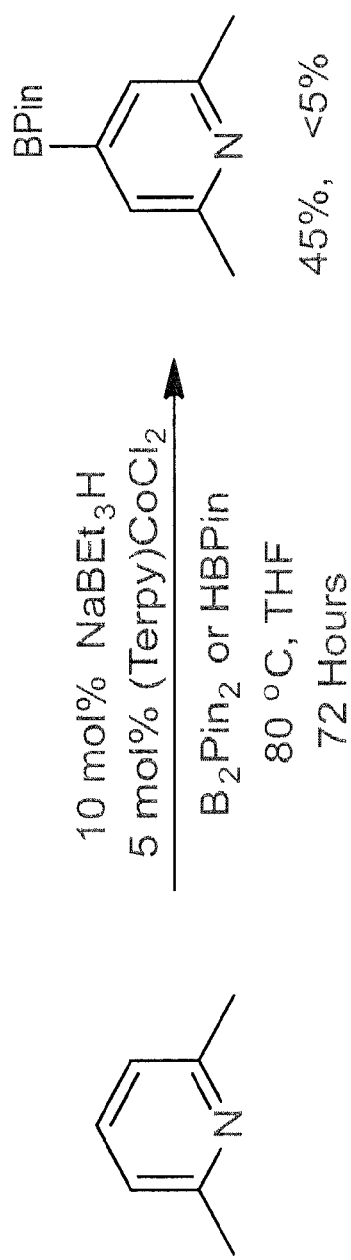
FIG. 6 illustrates a borylation reaction scheme according to one embodiment described herein.

Borylation with Co Catalyst 2,6 dimethyl pyridine was reacted with HBPin as illustrated in FIG. 6. The general procedure detailed in Example 5 was followed. The isolated compound was analyzed by $^1$H NMR and $^{13}$C NMR spectroscopy.

Various embodiments of the invention have been described in fulfillment of the various objects of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A method of providing a borylated product comprising:
providing a reaction mixture comprising an aliphatic compound or an aromatic compound, a borylation reagent and a cobalt complex having Formula (IV):

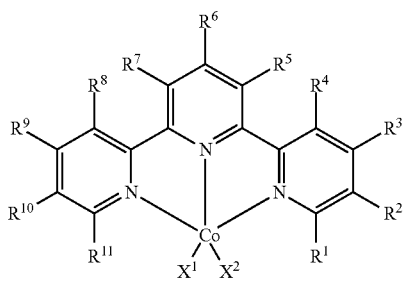

wherein $X^1$ and $X^2$ are independently selected from Group VIIA of the Periodic Table and $R^1$-$R^{11}$ are independently selected from the group consisting of hydrogen, alkyl, heteroalkyl, cycloalkyl, heterocycloalkyl, aryl, heteroaryl, alkyl-aryl and alkyl-heteroaryl, wherein the alkyl, heteroalkyl, cycloalkyl, heterocycloalkyl, aryl, heteroaryl, alkyl-aryl and alkyl-heteroaryl are optionally substituted with one or more substituents selected from the group consisting of $(C_1$-$C_{10})$-alkyl, $(C_1$-$C_{10})$-alkenyl, alkoxy, halo, hydroxy, $C(O)OR^{12}$, $NR^{13}R^{14}$, wherein $R^{12}$-$R^{14}$ are independently selected from the group consisting of hydrogen, $(C_1$-$C_{10})$-alkyl and $(C_1$-$C_{10})$-alkenyl;

adding an activator to the reaction mixture to activate the cobalt complex; and reacting the aliphatic compound or aromatic compound with the borylation reagent in the presence of the activated cobalt complex or a derivative of the activated cobalt complex.

2. The method of claim 1, wherein the reaction mixture comprises an aromatic compound having a five-membered aromatic ring or a six-membered aromatic ring.

3. The method of claim 1, wherein the borylation reagent is a boronic acid derivative.

4. The method of claim 1, wherein the borylation reagent is a diboron compound.

5. The method of claim 1, wherein the borylation reagent is selected from the group consisting of bis(pinacolato)diboron, bis(hexylene glycolato)diboron, bis(catecholato)diboron and bis(neopentyl glycolato)diboron.

6. The method of claim 1, wherein $X^1$ and $X^2$ and are chloro and $R^1$-$R^{11}$ are hydrogen.

7. The method of claim 1, wherein the reaction mixture comprises the aliphatic compound, and the aliphatic compound is saturated.

8. The method of claim 1, wherein the reaction mixture comprises the aliphatic compound, and the aliphatic compound is unsaturated.

9. The method of claim 1, wherein the reaction mixture comprises the aromatic compound.

10. The method of claim 9, wherein the aromatic compound is five-membered.

11. The method of claim 9, wherein the aromatic compound is six-membered.

12. The method of claim 1, wherein and $R^1$-$R^{11}$ are independently selected from the group consisting of hydrogen, alkyl, heteroalkyl, aryl and heteroaryl.

13. The method of claim 1, wherein and $R^1$-$R^{11}$ are independently selected from the group consisting of hydrogen, alkyl and aryl.

14. The method of claim 1, wherein and $R^1$-$R^{11}$ are independently selected from the group consisting of hydrogen and alkyl.

* * * * *